US012665085B2

(12) United States Patent
Lee

(10) Patent No.: US 12,665,085 B2
(45) Date of Patent: Jun. 23, 2026

(54) METHOD AND SYSTEM OF PROVIDING INFORMATION TO PREDICT BREAST RECONSTRUCTION SURGERY PROGNOSIS

(71) Applicant: SAMSUNG LIFE PUBLIC WELFARE FOUNDATION, Seoul (KR)

(72) Inventor: Kyeong Tae Lee, Seoul (KR)

(73) Assignee: SAMSUNG LIFE PUBLIC WELFARE FOUNDATION, Seoul (KR)

( * ) Notice: Subject to any disclaimer, the term of this patent is extended or adjusted under 35 U.S.C. 154(b) by 749 days.

(21) Appl. No.: 18/105,491

(22) Filed: Feb. 3, 2023

(65) Prior Publication Data

US 2023/0290507 A1 Sep. 14, 2023

(30) Foreign Application Priority Data

Feb. 7, 2022 (KR) ........................ 10-2022-0015817

(51) Int. Cl.
| | |
|---|---|
| *G16H 50/30* | (2018.01) |
| *A61B 34/10* | (2016.01) |
| *A61F 2/12* | (2006.01) |
| *G16H 20/40* | (2018.01) |
| *G16H 50/20* | (2018.01) |
| *G16H 50/70* | (2018.01) |

(52) U.S. Cl.
CPC .............. *G16H 50/20* (2018.01); *A61F 2/12* (2013.01); *G16H 50/70* (2018.01)

(58) Field of Classification Search
CPC ........ G16H 50/20; G16H 50/70; G16H 50/30; G16H 20/40; A61F 2/12; A61B 34/10; A61B 5/4842; A61B 5/4851; A61B 5/7275; A61B 2034/104; A61B 2034/105

See application file for complete search history.

(56) References Cited

FOREIGN PATENT DOCUMENTS

| | | | |
|---|---|---|---|
| KR | 10-2014-0125647 A | 10/2014 |
| KR | 10-1896545 B1 | 9/2018 |

OTHER PUBLICATIONS

Handel, Breast Implant Rupture: Causes, Incidence, Clinical Impact, and Management, Plastic and Reconstructive Surgery, vol. 132, No. 5, Nov. 2013 (Year: 2013).*

(Continued)

*Primary Examiner* — Vu Le
*Assistant Examiner* — Lei Zhao
(74) *Attorney, Agent, or Firm* — Dilworth IP, LLC

(57) ABSTRACT

A method of providing information for predicting the prognosis of breast reconstruction surgery and a system for predicting the prognosis of breast reconstruction surgery is provided. By using the method or system for providing information for predicting the prognosis of breast reconstruction surgery according to one specific example of the present invention, it is possible to predict the possibility of implant rupture in a subject who has undergone or is scheduled to undergo two-stage breast reconstruction surgery, and it is possible to prepare an appropriate treatment according to this prediction, and to adjust the interval between breast reconstruction surgeries so as to lower the possibility of implant rupture. In addition, it is possible to provide information so that an implant with a low possibility of rupture may be selected.

15 Claims, 8 Drawing Sheets

COLLECT CLINICAL DATA

CALCULATE PATTERN BASED ON INTERVAL BETWEEN BREAST RECONSTRUCTION SURGERIES, TYPE OF IMPLANT IMPLANTED, AND WHETHER IPLANT HAS RUPTURED

PREDICT PROGNOSIS OF BREAST RECONSTRUCTION SURGERY BY PREDICTING THE POSSIBILITY OF IMPLANT RUPTURE BY APPLYING, TO PATTERN, INTERVAL BETWEEN BREAST RECONSTRUCTION SURGERIES OR TYPE OF IMPLANT FOR A SUBJECT

(56)            References Cited

OTHER PUBLICATIONS

Spear, Natrelle Round Silicone Breast Implants: Core Study Results at 10 Years, Plastic and Reconstructive Surgery, vol. 133, No. 6, Jun. 2014 (Year: 2014).*
Bengtson, Style 410 Highly Cohesive Silicone Breast Implant Core Study Results at 3 Years, Plastic and Reconstructive Surgery, December Supplement 1, vol. 120, No. 7 Suppl. 1, 2007 (Year: 2007).*
Holmich, The Diagnosis of Silicone Breast-Implant Rupture Clinical Findings Compared With Findings at Magnetic Resonance Imaging, Annals of Plastic Surgery, vol. 54, No. 6, Jun. 2005 (Year: 2005).*

Haws, Sientra Portfolio of Silimed Brand Shaped Implants with High-Strength Silicone Gel: A 5-Year Primary Augmentation Clinical Study Experience and a Postapproval Experience—Results from a Single-Surgeon 108-Patient Series, Plastic and Reconstructive Surgery, July Supplement 2014 (Year: 2014).*
Bae, Juyoung, et al., Predictors for Implant Rupture in Two-Stage Tissue Expander-Based Breast Reconstruction: A Retrospective Cohort Study, Ann. Surg. Oncol., pp. 1100-1108, Sep. 30, 2021.
Goldhirsch, Aron, et al., Meeting Highlights: International Consensus Panel on the Treatment of Primary Breast Cancer, Journal of Clinical Oncology, vol. 19, No. 18 Sep. 15, 2001: pp. 3817-3827.
Bae, Juyoung, et al., Predictors for Implant Rupture in Two-Stage Tissue Expander-Based Breast Reconstruction: A Retrospective Cohort Study, Ann. Surg. Oncol., [online summary] 1 page, Sep. 30, 2021.

* cited by examiner

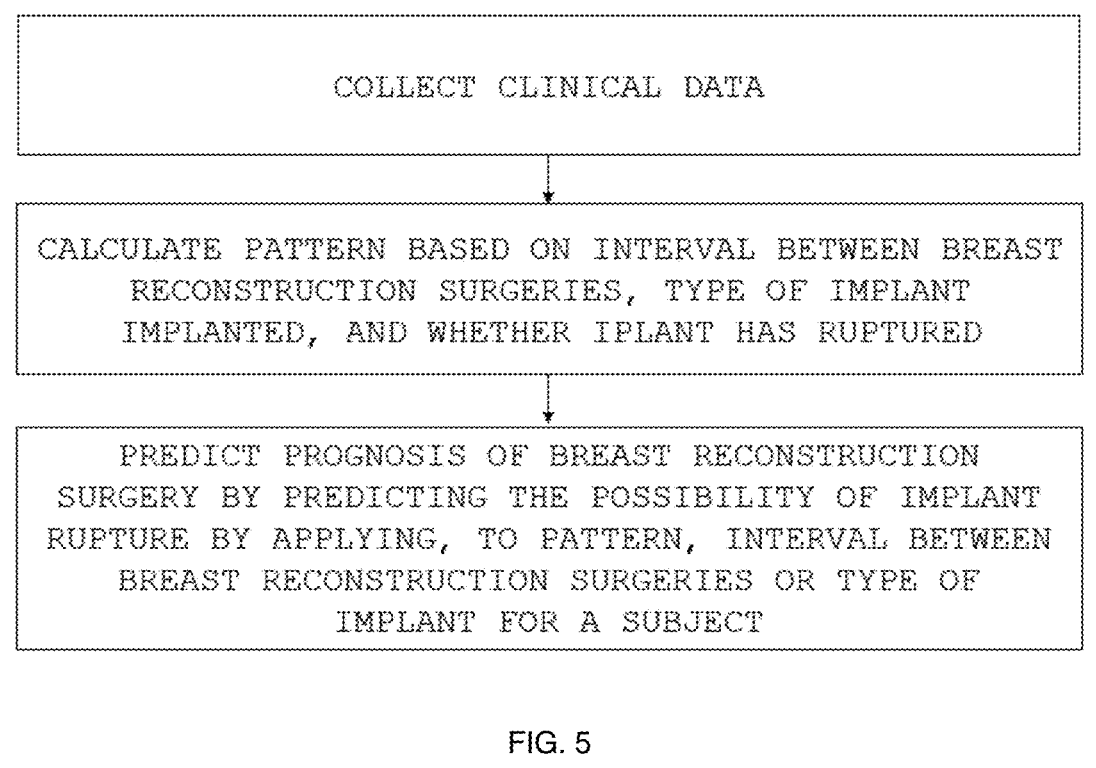

COLLECT CLINICAL DATA

CALCULATE PATTERN BASED ON INTERVAL BETWEEN BREAST
RECONSTRUCTION SURGERIES, TYPE OF IMPLANT
IMPLANTED, AND WHETHER IPLANT HAS RUPTURED

PREDICT PROGNOSIS OF BREAST RECONSTRUCTION
SURGERY BY PREDICTING THE POSSIBILITY OF IMPLANT
RUPTURE BY APPLYING, TO PATTERN, INTERVAL BETWEEN
BREAST RECONSTRUCTION SURGERIES OR TYPE OF
IMPLANT FOR A SUBJECT

FIG. 5

METHOD AND SYSTEM OF PROVIDING INFORMATION TO PREDICT BREAST RECONSTRUCTION SURGERY PROGNOSIS

FIELD OF THE INVENTION

The present invention relates to a method and a system for providing information for predicting the prognosis of breast reconstruction surgery.

BACKGROUND OF THE INVENTION

Breast cancer is the most common cancer in women and is the second most fatal cancer. In 2001, the prevalence of breast cancer was 90 to 100 per 100,000 in the United States and 50 to 70 per 100,000 in Europe. The incidence of this disease is gradually increasing worldwide. Risk factors for breast cancer include race, age, mutations in tumor suppressor genes BRCA1, BRCA2, and p53, etc. Alcohol intake, high-fat diet, lack of exercise, exogenous postmenopausal hormones, and ionizing radiation also increase the risk of breast cancer. Estrogen receptor (ER–) and progesterone receptor (PR–) negative breast cancer, a large tumor size, a high-grade cytology result, and an age under 35 are associated with a poor prognosis (Goldhirsch et al. (2001). J. Clin. Oncol. 19: 3817-27).

The most essential treatment for breast cancer is a surgical operation to remove a tumor, and adjuvant therapy, such as prior chemotherapy using drugs before surgery, radiotherapy to prevent cancer recurrence after surgery, anticancer chemotherapy, anticancer hormone therapy, or the like, is performed depending on the state of the tumor. As for the adjuvant therapy, the type and order of therapy are determined according to the patient's age, presence or absence of menopause, microscopic characteristics of breast cancer, degree of metastasis, patient's symptoms, and other health conditions.

In breast cancer surgery, when cancer is present locally, the breast may be preserved by removing only the cancer and part of the normal tissue around the cancer, and when cancer has invaded lymph nodes or other tissue, the breast is completely removed and then breast reconstruction surgery may be performed to restore the breast. Reconstruction surgery after a mastectomy is divided into immediate reconstruction surgery, which is performed simultaneously with a mastectomy, and delayed reconstruction surgery, which is performed after a sufficient period of time has elapsed after surgery, depending on the reconstruction period. As the reconstruction surgery after a mastectomy, there are insertion surgery in which an implant or a tissue expander and an implant are implanted, and skin flap surgery in which autologous tissue such as skin, muscle, fat, and the like of the back or abdomen is used. The timing and method of such reconstruction surgery are determined in consideration of the patient's condition, mastectomy method, stage of breast cancer, presence or absence of metastasis, presence or absence of adjuvant therapy, and the like. Breast cancer patients who have undergone mastectomies experience not only physical changes but also psychological side effects such as low self-esteem, depression, and the like due to loss of femininity. In the case of patients who have undergone reconstruction surgery to restore the breast at the same time as a mastectomy, immediate reconstruction surgery is preferred because it has been shown to provide significant benefits to the patients in both psychological aspects and overall quality of life after treatment. Immediate reconstruction surgery includes a stage 1 surgery in which insertion of a tissue expander is performed together with total mastectomy, followed by a stage 2 surgery of removing the tissue expander after completion of expansion of the tissue expander and implanting an implant.

Various types of complications associated with an implant implanted in two-stage breast reconstruction surgery may occur. Rupture of the implanted implant is one of the most worrisome complications. Rupture of the implant can be classified into intracapsular rupture and extracapsular rupture. The intracapsular rupture means that the silicone gel leaks out due to the rupture of the implant but remains in the shell surrounding the implant, and the extracapsular rupture means that the silicone gel leaks out of the capsule of the implant. The ruptured silicone implant may cause various side effects ranging from small side effects such as deformation of the shape of the breast in the case of intracapsular rupture to systemic symptoms that may occur in the case of extracapsular rupture. Thus, when the implant ruptures, the patient's physical appearance may be changed, reducing the patient's satisfaction, and reoperation for removing or exchanging the implant may be required, which may increase morbidity.

A number of current studies conducted on implant rupture have not yielded significant results in identifying the predictor, and have suggested the conclusion that damage caused by external forces or surgical instruments can cause implant shell fatigue, which can cause implants to rupture. However, there is no clinical evidence yet to support this conclusion.

Implants that are implanted in the stage 2 surgery are produced as various products by various manufacturers such as Mentor, Allergan, and BellaGel. There has been no study on the effect of implant type on the possibility of implant rupture.

Meanwhile, in the case of patients undergoing two-stage breast reconstruction surgery, which is currently being performed most frequently, adjuvant chemotherapy is usually performed between the stage 1 surgery and the stage 2 surgery, and the interval between the stage 1 surgery and the stage 2 surgery varies depending on whether or not such adjuvant therapy is performed. There has been no study on the effect of the interval between the surgeries on subsequent rupture of the implant.

Therefore, it is necessary to identify the type of implant or the interval between the stage 1 and stage 2 surgeries, which is a factor influencing the occurrence of implant rupture.

SUMMARY OF THE INVENTION

The present invention is directed to providing a method of providing information to predict the prognosis of a patient who has undergone breast reconstruction surgery after a mastectomy.

The present invention is also directed to providing a system for predicting the prognosis of a patient who has undergone breast reconstruction surgery after a mastectomy.

According to an aspect of the present invention, there is provided a method of providing information to predict a prognosis of breast reconstruction surgery, comprising collecting clinical data; calculating a pattern including the same result by classifying the clinical data on the basis of interval between breast reconstruction surgeries, type of implant implanted, and whether the implant has ruptured; and predicting possibility of implant rupture in a subject by applying an interval between breast reconstruction surgeries or a type of implant implanted, among clinical data of the subject to the calculated pattern.

As used in the present invention, "breast reconstruction surgery" refers to surgery performed to restore a shape of a breast after the breast is removed in order to treat breast cancer, and it is possible to restore the breast by implanting an implant or restore the breast with autologous tissue by moving some of the muscle and skin from the patient's abdomen or back, etc.

As used in the present invention, "prognosis" means determining the presence or absence of recurrence, metastasis, complications, drug reactivity, resistance, etc. of the subject before/after treatment for subjects who have not yet been diagnosed or have been diagnosed. In the present invention, "prognosis" means predicting whether the possibility of complication occurrence after breast reconstruction surgery is high using clinical data of patients who have undergone breast reconstruction surgery.

According to one specific example of the present invention, the breast reconstruction surgery may be a two-stage breast reconstruction surgery comprising inserting a tissue expander; and exchanging the tissue expander for an implant.

The interval between breast reconstruction surgeries refers to the interval between a stage 1 surgery in which total mastectomy and tissue expander insertion are performed and a stage 2 surgery in which the tissue expander is exchanged for an implant.

The collecting clinical data is a process of obtaining information necessary for prognosis prediction. The clinical data may be information related to a patient who has undergone breast reconstruction surgery after mastectomy. Specifically, the clinical data may be information on age, body mass index (BMI), the presence or absence of diabetes, the presence or absence of hypertension, smoking or not, the presence or absence of adjuvant chemotherapy, the presence or absence of neoadjuvant chemotherapy, the presence or absence of adjuvant radiotherapy, the presence or absence of hormone therapy, a tissue expander and implant used in breast reconstruction surgery, and a result after breast reconstruction surgery.

According to one specific example of the present invention, in the patient who has undergone two-stage breast reconstruction surgery, information related to the stage 1 surgery may be information on the type of mastectomy, the weight of the resected specimen, the type of tissue expander, whether an artificial dermal matrix (ADM) is used, and the amount of initial expansion. Information related to the stage 2 surgery may be information on a manufacturer and a product in relation to the type of implant implanted, and information about whether measures to balance both breasts are implemented.

The implant may be of various types, and the manufacturer thereof may be Mentor, Allergan, or BellaGel. The implant may be classified based on type into round and shape, and classified by surface texture into smooth and textured.

In addition, the clinical data may also include information on the temporal interval between the stage 1 and stage 2 surgeries.

The calculating a pattern including the same result by classifying the clinical data on the basis of interval between breast reconstruction surgeries, type of implant implanted, and whether the implant has ruptured, is a process of calculating a pattern, that is, a prognostic prediction model, which corresponds to whether the implant ruptures depending on the interval between breast reconstruction surgeries and the type of implant implanted, based on the interval between breast reconstruction surgeries, the type of implant implanted, and whether the implant has ruptured, among the clinical data collected to predict the prognosis of breast reconstruction surgery.

The predicting possibility of implant rupture in a subject by applying an interval between breast reconstruction surgeries or a type of implant implanted, among clinical data of the subject to the generated calculated pattern, is a step of predicting the possibility of implant rupture in a subject in need of prognosis prediction by comparing, with the calculated pattern, with information on the interval between breast reconstruction surgeries or the type of implant implanted, among clinical data for the subject.

The subject may be a breast cancer patient who has undergone two-stage breast reconstruction surgery after mastectomy.

Rupture of the implant may be classified into intracapsular rupture and extracapsular rupture. The intracapsular rupture means that the silicone gel leaks out due to the rupture of the implant but remains in the shell surrounding the implant, and the extracapsular rupture means that the silicone gel leaks out of the capsule of the implant.

According to one specific example of the present invention, the interval between breast reconstruction surgeries may be 6 months or less or more than 6 months.

According to one specific example of the present invention, the predicting the possibility of implant rupture may include predicting that the possibility of implant rupture is high when the interval between breast reconstruction surgeries is 6 months or less.

The interval between breast reconstruction surgeries operations may vary from patient to patient due to the timing of completion of oncological treatment such as adjuvant chemotherapy, which is performed after the stage 1 surgery.

According to one example of the present invention, it was shown in the Kaplan-Meier analysis that the period of time during which the implant lasted without rupture was significantly shorter when the interval between breast reconstruction surgeries for the subject was 6 months or less than when the interval between breast reconstruction surgeries was more than 6 months (p=0.006) (FIG. 3).

According to one specific example of the present invention, the type of the implant may be any one implant selected from the group consisting of Mentor textured shape, Mentor smooth round, Allergan textured shape, Allergan textured round, Allergan smooth round, BellaGel textured shape, and BellaGel smooth round.

The type of the implant may be classified according to form stability into a non-form-stable $4^{th}$ generation implant (Allergan textured round or Allergan smooth round) or a form-stable $5^{th}$ generation implant, and is selected by a reconstruction surgeon through consultation with a patient when planning breast reconstruction surgery.

According to one specific example of the present invention, the predicting the possibility of implant rupture may comprise predicting that the possibility of implant rupture is high when the type of the implant is an Allergan textured round or an Allergan smooth round.

According to one example of the present invention, the possibility of implant rupture significantly increased when an Allergan Biocell textured round implant was used compared to when Mentor memory-shape implant was used (p=0.037, HR 10.520, 95% CI 1.150-96.242). In addition, it was shown that, even when the Allergan smooth round implant was used, the possibility of implant rupture significantly increased (HR 13.257, 95% CI 1.463-120.127, p=0.022).

According to this method of providing information for predicting the prognosis of breast reconstruction surgery, it is possible to provide information so that the possibility of implant rupture depending on the interval between the stage 1 and stage 2 surgeries or the type of implant in the two-stage breast reconstruction surgery may be predicted, an appropriate treatment according to this prediction may be prepared, an execution schedule of the stage 2 surgery may be planned so that the possibility of implant rupture will be low, and the type of implant may be selected.

The above-described method for providing information for predicting the prognosis of breast reconstruction surgery may be implemented by a system using a computer device.

Another aspect of the present invention provides a system for predicting the prognosis of breast reconstruction surgery.

More specifically, referring to FIG. 6, a system 100 for predicting the prognosis of breast reconstruction surgery comprises an input unit 110 configured to receive clinical data; a pre-processing unit 120 configured to calculate a pattern including the same result by classifying the clinical data on the basis of interval between breast reconstruction surgeries, type of implant implanted, and whether the implant has ruptured; and an analysis unit 130 configured to predict possibility of implant rupture in a subject by applying an interval between breast reconstruction surgeries or a type of implant implanted, among clinical data of the subject to the calculated pattern.

Descriptions overlapping with the foregoing will be omitted in order to avoid excessive complexity.

The input unit 110 receives clinical data and medical records from a medical record server or the like. The clinical data may include diagnostic information on the interval between breast reconstruction surgeries, the type of implant implanted, and whether the implant has ruptured after the stage 2 surgery, for patients who have undergone breast reconstruction surgery after mastectomy.

According to one specific example of the present invention, the breast reconstruction surgery may be a two-stage breast reconstruction surgery comprising inserting a tissue expander; and exchanging the tissue expander for an implant.

The pre-processing unit 120 calculates a pattern, that is, a prognostic prediction model, including the same result by classifying the clinical data on the basis of interval between breast reconstruction surgeries, type of implant implanted, and whether the implant has ruptured.

According to one specific example of the present invention, the interval between breast reconstruction surgeries may be 6 months or less or more than 6 months.

According to one specific example of the present invention, it may be predicted that the possibility of implant rupture is high when the interval between breast reconstruction surgeries is 6 months or less.

According to one specific example of the present invention, the type of the implant may be any one implant selected from the group consisting of Mentor textured shape, Mentor smooth round, Allergan textured shape, Allergan textured round, Allergan smooth round, BellaGel textured shape, and BellaGel smooth round.

According to one specific example of the present invention, it may be predicted that the possibility of implant rupture is high when the type of the implant is an Allergan textured round or an Allergan smooth round.

In the present invention, the possibility of implant rupture may be analyzed by classifying various information on the interval between breast reconstruction surgeries, the type of implant implanted, and whether or not the implant has ruptured, in order to calculate a pattern.

The analysis unit 130 analyzes the pattern calculated by the pre-processing unit 120 and the interval between breast reconstruction surgeries or the type of implant, which is input to the input unit 110, thereby predicting the possibility of implant rupture in a patient who has undergone or is scheduled to undergo two-stage breast reconstruction surgery.

For example, in a subject who has undergone two-stage breast reconstruction surgery, it may be predicted that, when the interval between the stage 1 and stage 2 surgeries is 6 months or less, the possibility of implant rupture will be high, and when the interval is more than 6 months, the possibility of implant rupture will be low.

According to one specific example of the present invention, the analysis unit 130 may predict that the possibility of implant rupture is high when the interval between the stage 1 and stage 2 surgeries for the subject is 6 months or less.

This system 100 for predicting the prognosis of breast reconstruction surgery comprising the input unit 110, the pre-processing unit 120, and the analysis unit 130 may further comprise a result display unit 140.

According to one specific example of the present invention, the system 100 may further comprise a display unit configured to output the result of predicting the possibility of implant rupture of a subject in the analysis unit.

The display unit 140 may be a separate display screen or may be a certain space in an existing computer device in which the prognosis prediction system 100 is stored.

Referring to FIG. 7 or 8, the interval between breast reconstruction surgeries or the type of implant implanted for a subject who is to be predicted for the prognosis of breast reconstruction surgery is input to the system 100 for predicting the prognosis of breast reconstruction surgery, and the system 100 may suggest the possibility of implant rupture depending on the interval between breast reconstruction surgeries and the type of implant implanted, which has been input thereto.

The system 100 for predicting the prognosis of breast reconstruction surgery according to the present invention may be stored in a recording medium by driving one or more programs, and may be implemented by a device such as a computer or server.

The program may include codes coded in various computer languages that may be executed by a processor of a computer or server. The codes may include codes such as functions defining functions necessary for predicting the prognosis of breast reconstruction surgery and control codes capable of controlling the codes.

In addition, the recording medium in which the program is stored is a medium readable by a computer or server, and examples thereof include ROM, RAM, CD-ROM, magnetic tape, floppy disk, optical disk, USB memory, SD card, micro SD card, etc., without being limited thereto.

The system of the present invention is preferably implemented as a single hardware device, but, if necessary, may be implemented as an embedded device accommodated in an existing hardware device or as an application downloaded and installed in the form of software.

By using the method or system for providing information for predicting the prognosis of breast reconstruction surgery according to one specific example of the present invention, it is possible to predict the possibility of implant rupture in a subject who has undergone or is scheduled to undergo two-stage breast reconstruction surgery, and it is possible to prepare an appropriate treatment according to this prediction, and to adjust the interval between the stage 1 surgery and the stage 2 surgery in order to lower the risk of implant rupture. In addition, it is possible to provide information so that an implant with a low possibility of rupture may be selected.

BRIEF DESCRIPTION OF DRAWINGS

FIG. 5 is a flow chart showing a method for providing information for predicting the prognosis of breast reconstruction surgery according to one specific example of the present invention.

DETAILED DESCRIPTION OF THE INVENTION

Figure 1:
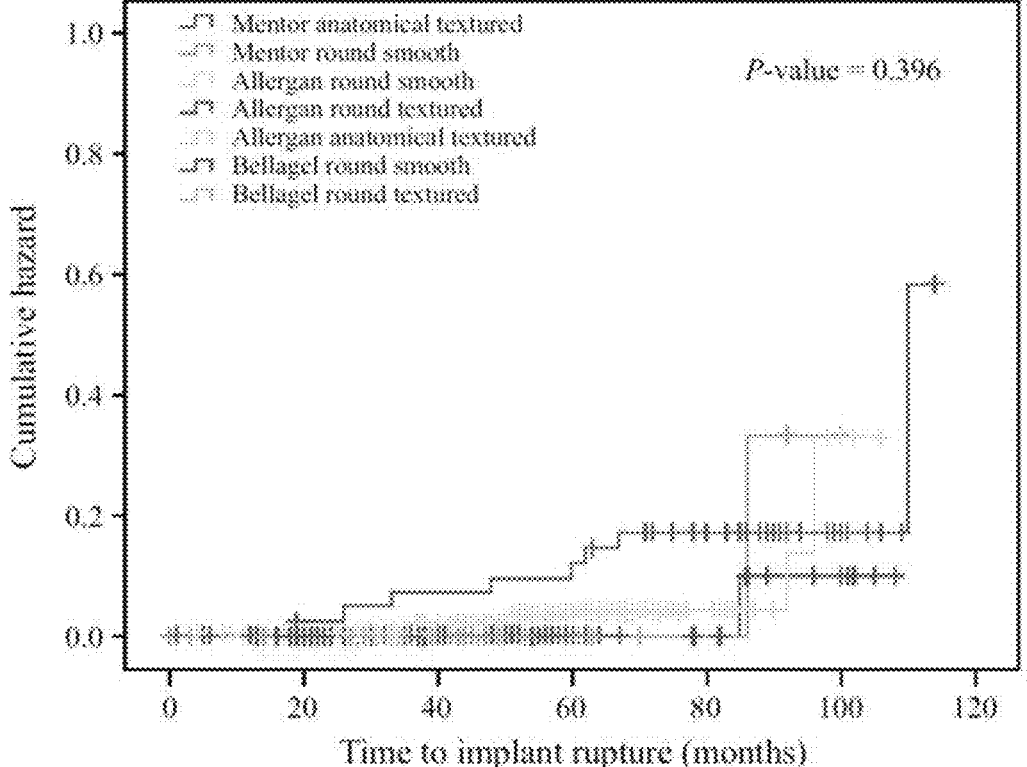
FIG. 1 shows the cumulative incidence rate of implant rupture depending on the type of implant.

Hereinafter, one or more embodiments will be described in more detail with reference to examples. However, these examples are for explaining one or more embodiments in detail, and the scope of the present invention is not limited to these examples.

Hereinafter, a process for predicting the possibility of implant rupture after breast reconstruction surgery according to this example will be described.

1. Preparation for Study 1-1. Study Population

Information was retrospectively collected from a database for patients who underwent two-stage breast reconstruction surgery (including tissue expander insertion and silicone implant exchange) together with total mastectomy between 2010 and 2016. The following cases were excluded for the homogeneity of the study population: cases who underwent breast reconstruction surgery with implant insertion immediately after total mastectomy; cases who underwent breast reconstruction surgery using an implant together with an autologous flap; and cases who underwent delayed breast reconstruction surgery after total mastectomy. This study was approved by the Institutional Review Board of Samsung Medical Center.

1-2. Collection of Basic Information

Patient- and surgery-related information (information related to total mastectomy, stage 1 surgery and stage 2 surgery) was collected retrospectively on a monthly basis. Information on the interval between stage 1 surgery and stage 2 surgery (hereafter referred to as "interval between breast reconstruction surgeries") and post-surgery procedures including cancer treatment was also collected.

Essentially, information on whether the implant ruptured after surgery was collected. Since breast MRI (Magnetic Resonance Imaging) examinations have high specificity and sensitivity in detecting whether an implant implanted into the breast has ruptured, patients who underwent silicone implant insertion at Samsung Medical Center were instructed to undergo MRI examinations at two-year intervals.

In addition, for at least 5 years after surgery, ultrasonography was performed by surgeons every 6 months for invasive cancer patients and every 12 months for non-invasive cancer patients for regular cancer surveillance after surgery. In the case of patients with advanced tumors, a chest CT (computed tomography) examination was performed every year. When signs of implant rupture were found in the result image of various examinations including ultrasonography, a referral was made to a plastic surgeon for detailed examination and medical treatment.

1-3. Collection of Information on Implant Rupture

Patients with signs of implant rupture were subjected to a physical examination and a breast MRI examination, and instructed to receive medical treatment by a plastic surgeon. When the conducted examination indicated that implant rupture was confirmed or suspected, implant removal or exchange was planned in consideration of the patient's cancer treatment schedule and general health condition.

The period during which the implant ruptured was defined as the period from the day when the stage 2 surgery was performed to the day when implant rupture was found on the breast MRI.

1-4. Statistical Analysis

Patients with ruptured implants and patients with non-ruptured implants were compared based on patient-related variables and surgery-related variables. Pearson's Chi square test or Fisher's exact test were used to analyze categorical variables, and Student's t-test or Mann-Whitney t-test was used to analyze continuous variables. Kaplan-Meier analysis was used to create a graph for the period during which the implant lasted without rupture and to make comparison with log-rank tests for each categorical variable. Univariate and multivariate Cox regression analyses to determine hazard ratios (HRs) and corresponding 95% confidence intervals (CIs) were performed to evaluate the independent influence of variables related to implant rupture results. Variables with a p value<0.15 in univariate analysis were included in multivariate analysis. A p value<0.05 was considered statistically significant. All statistical analyzes were performed using SPSS version 20 (IBM Corporation, USA).

2. Study Results 2-1. Results of Information Collection

During the study period, 827 cases (790 patients) underwent immediate two-stage breast reconstruction surgery. Thereamong, 744 patients representing 797 cases were included as the final analysis subjects. Thereamong, 53 patients underwent bilateral breast reconstruction surgery.

The mean age was 43.6 years (range: 18 to 66 years) and the mean BMI was 22.0 kg/m$^2$ (range: 15.1 to 33.7 kg/m$^2$). The median value of the postoperative follow-up period from the time of total mastectomy and stage 1 surgery and the median value of the postoperative follow-up period from the time of stage 2 surgery were 53.0 months and 43.0 months, respectively. The median value of the interval from the time of total mastectomy and stage 1 surgery to the time of stage 2 surgery was 10 months.

All of the implanted implants were silicone implants, and there was no case in which saline implants were used. The use rates of textured implants and smooth implants were 60.8% and 39.2%, respectively, indicating that textured implants were used more frequently. The use rates of shape implants and round implants were 54.0% and 46.0%, respectively, indicating that shape implants were used more frequently. Referring to Table 1 below, the use rates of implant products were as follows: 41.3% for Mentor MemoryShape Contour Profile Gel) implant, 28.9% for Allergan Smooth Round Gel implant, 11.4% for Allergan Natrelle 410 Anatomical Gel implant, 18.5% for Mentor Memory Gel implant, 5.4% for Allergan Textured Round Gel implant, and the remainder for the other products.

TABLE 1

| Manu-facturer | Texture and shape (product name) | Number of patients (%) |
|---|---|---|
| Mentor | Textured shape implant (MemoryShape) | 329 (41.3) |
| | Smooth round implant (Memory Gel) | 64 (18.5) |

TABLE 1-continued

| Manu-facturer | Texture and shape (product name) | Number of patients (%) |
|---|---|---|
| Allergan | Textured shape implant (Natrelle 410 Anatomical Gel) | 91 (11.4) |
| | Textured round implant (Biocell Textured Style 110, 115 and 120) | 43 (5.4) |
| | Smooth round implant (Style 10, 40 and 45) | 230 (28.9) |
| BellaGel | Smooth round implant | 40 (5.0) |
| | Textured shape implant | 3 (0.4) |

During the postoperative follow-up period, implant rupture occurred in 22 cases (3.0%). Only one patient complained of a change in the shape of the reconstructed breast before being diagnosed with implant rupture, and the other patients did not show any symptoms or signs related to the implant implanted into the breast before being diagnosed with implant rupture.

The results of MRI before surgery indicated that one case showed signs of both intracapsular and extracapsular rupture, and the remaining 21 cases showed only intracapsular rupture. The breast MRI results indicated that all of the patients with signs of implant rupture had ruptured implants during implant removal or exchange surgery. The 2-year cumulative and 5-year cumulative incidence rates of implant rupture were 0.3% and 3.1%, respectively. The median value of the interval between stage 2 surgery and implant rupture was 51.5 months (range: 12 to 110 months). Table 2 below shows the results of comparing patient-related variables and surgery-related variables between patients with ruptured implants and patients with non-ruptured implants.

TABLE 2

| Variables | Sum (n = 797) | Ruptured cases (n = 22) | Non-ruptured cases (n = 775) | P value |
|---|---|---|---|---|
| | Patient-related variables | | | |
| Age at stage 2 surgery | 43.6 (±7.4) | 44.5 (±5.5) | 43.5 (±7.3) | 0.487 |
| BMI (kg/m2) at stage 2 surgery | 22.0 (±2.8) | 22.1 (±3.7) | 22.0 (±2.8) | 0.722 |
| Diabetes | 8 | 0 | 8 (100.0%) | 0.632 |
| Hypertension | 31 | 1 (3.2%) | 30 (96.8%) | 0.872 |
| Smokers | 21 | 0 | 21 (100.0%) | 0.434 |
| | Variables related to stage 1 surgery | | | |
| | Type of mastectomy | | | 0.695 |
| NSM | 259 | 8 (3.1%) | 251 (96.9%) | |
| Non-NSM | 538 | 14 (2.6%) | 524 (97.4%) | |
| Weight of specimen | 352.4 (±173.7) | 311.5 (±208.5) | 353.6 (±172.6) | 0.064 |
| | Type of tissue expander | | | 0.633 |
| Siltex micro textured tissue expander | 658 | 19 (2.9%) | 639 (97.1%) | |
| Biocell macro textured tissue expander | 139 | 3 (2.2%) | 136 (97.8%) | |
| Size of tissue expander | 389.5 (± 91.8) | 386.4 (±94.1) | 389.6 (±91.8) | 0.836 |
| | Whether artificial dermis matrix (ADM) was used | | | 0.008 |
| Used | 470 | 7 (1.5%) | 463 (98.5%) | |
| Not used | 326 | 15 (4.6%) | 311 (95.4%) | |
| Amount of initial expansion | 146.9 (±96.5) | 140.2 (±76.5) | 147.1 (±97.0) | 0.867 |

TABLE 2-continued

| Variables | Sum (n = 797) | Ruptured cases (n = 22) | Non-ruptured cases (n = 775) | P value |
|---|---|---|---|---|
| Variables related to stage 2 surgery | | | | |
| Size of implant | 330.4 (±103.1) | 318.3 (±110.0) | 330.7 (±103.0) | 0.649 |
| Type of implant | | | | |
| Manufacturer | | | | <0.001 |
| Mentor | 390 | 2 (0.5%) | 388 (99.5%) | |
| Allergan | 364 | 19 (5.2%) | 345 (94.8%) | |
| BellaGel | 43 | 1 (2.3%) | 42 (97.7%) | |
| Product | | | | <0.001 |
| Mentor textured shape implant | 329 | 1 (0.3%) | 328 (99.7%) | |
| Mentor smooth round implant | 61 | 1 (1.6%) | 60 (98.4%) | |
| Allergan textured shape implant | 91 | 3 (3.3%) | 88 (96.7%) | |
| Allergan textured round implant | 43 | 8 (18.6%) | 35 (81.4%) | |
| Allergan smooth round implant | 230 | 8 (3.5%) | 222 (96.5%) | |
| BellaGel textured shape implant | 3 | 0 | 3 (100.0%) | |
| BellaGel smooth round implant | 40 | 1 (2.5%) | 39 (97.5%) | |
| Measures to balance both breasts (contralateral) | | | | 0.028 |
| Breast augmentation surgery | 172 | 10 (5.8%) | 162 (94.2%) | |
| Mastopexy | 15 | 1 (6.7%) | 14 (93.3%) | |
| Breast reduction surgery | 16 | 0 | 16 (100.0%) | |
| Adjuvant radiotherapy | 121 | 1 (0.8%) | 120 (99.2%) | 0.159 |
| Neoadjuvant chemotherapy | 37 | 0 | 37 (100.0%) | 0.294 |
| Adjuvant chemotherapy | 315 | 6 (1.9%) | 309 (98.1%) | 0.233 |
| Hormone therapy | 643 | 20 (3.1%) | 623 (96.9%) | 0.218 |
| administration of tamoxifen | 602 | 21 (3.5%) | 581 (96.5%) | 0.028 |
| Interval between stage 1 and stage 2 surgeries* | 10.0 | 6.0 | 10.0 | <0.001 |

*Median value
NSM: Nipple-sparing mastectomy
ADM: Acellular dermal matrix

Patient-related variables and variables related to stage 1 surgery were generally similar except for the use rate of artificial dermis matrix (ADM). Regarding variables related to the stage 2 surgery, there was a big difference in the type of implant used and the performance rate of measures to balance both breasts, depending on the specific profile or manufacturer of the implant. There was also a significant difference in the interval between breast reconstruction surgeries, and the interval was shorter in the case of implant rupture. In the Kaplan-Meier analysis, there were no categorical variables showing a significant difference for the period during which the implant lasted without rupture, including reconstructive surgeon, whether artificial dermis matrix was used, type of tissue expander, type of mastectomy, type of implant (by manufacturer and specific product), measures to balance both breasts, and whether adjuvant radiotherapy, chemotherapy, and hormone therapy were performed. The use of the Allergan round textured implant showed a higher cumulative rupture rate than the use of the other implants, but there was no statistically significant difference (FIG. 1). In order to adjust the effect of the potential learning curve, the cases were divided into two groups based on the timing of stage 2 surgery: a group in which stage 2 surgery was performed between 2010 and 2014, and a group in which stage 2 surgery was performed between 2015 and 2018. However, there was no significant difference in the incidence rate of implant rupture between the two groups.

2-1. Univariate or Multivariate Analysis to Identify Predictors of Implant Rupture 2-2-1. Interval Between Breast Reconstruction Surgeries In univariate analysis, it was shown that the interval between stage 1 and stage 2 surgeries was marginally significant with the incidence of implant rupture (p=0.052). That is, patients with a relatively long interval between surgeries had a lower possibility of implant rupture than patients with a relatively short interval between surgeries (HR 0.849, 95% CI 0.720-1.001). This correlation was more pronounced in subsequent multivariate analysis (HR 0.815, 95% CI 0.674-0.985, p=0.034) (Table 3).

TABLE 3

| Variables | Univariate | | Multivariate | |
|---|---|---|---|---|
| | P value | HR (95% CI) | P value | HR (95% CI) |
| Patient-related variables | | | | |
| Age | 0.586 | 1.017 (0.958-1.080) | | |
| BMI | 0.367 | 1.071 (0.923-1.244) | | |

TABLE 3-continued

| Variables | Univariate | | Multivariate | |
| | P value | HR (95% CI) | P value | HR (95% CI) |
| --- | --- | --- | --- | --- |
| Diabetes | 0.732 | 0.048 (0-) | | |
| Hypertension | 0.523 | 1.931 (0.256-14.564) | | |
| Smokers | 0.648 | 0.048 (0-) | | |
| Reconstruction surgeons | | | | |
| Doctor A | Ref. | | | |
| Doctor B | 0.232 | 2.016 (0.639-6.365) | | |
| Doctor C | 0.218 | 2.263 (0.728-7.033) | | |
| Doctor D | 0.885 | 0.848 (0.091-7.892) | | |
| Variables related to stage 1 surgery | | | | |
| Type of mastectomy | | | | |
| Non-NSM | Ref. | | | |
| NSM | 0.706 | 0.839 (0.338-2.087) | | |
| Weight of specimen | 0.880 | 1.000 (0.997-1.002) | | |
| Type of tissue expander | | | | |
| Siltex micro textured tissue expander | Ref. | | | |
| Biocell macro textured tissue expander | 0.226 | 2.252 (0.605-8.382) | | |
| Size of tissue expander | 0.895 | 1.000 (0.995-1.006) | | |
| Use Of artificial dermal matrix | 0.615 | 0.771 (0.280-2.124) | | |
| Amount of initial expansion | 0.983 | 1.000 (0.995-1.005) | | |
| Variable related to stage 2 surgery | | | | |
| Period of surgery | | | | |
| Period 1* | Ref. | | Ref. | |
| Period 2** | 0.942 | 0.957 (0.291-3.143) | 0.074 | 3.403 (0.889-13.034) |
| Size of implant | 0.709 | 0.999 (0.994-1.004) | | |
| Type of implant | | | | |
| Mentor textured shape implant | Ref. | | Ref. | |
| Mentor smooth round implant | 0.276 | 4.701 (0.291-76.045) | 0.264 | 5.005 (0.296-84.563) |
| Allergan textured shape implant | 0.099 | 5.928 (0.715-49.188) | 0.088 | 7.659 (0.736-79.658) |
| Allergan textured round implant | 0.037 | 10.520 (1.150-96.242) | 0.016 | 18.867 (1.712 207.890) |
| Allergan smooth round implant | 0.137 | 5.675 (0.575-56.011) | 0.022 | 13.257 (1.463 120.127) |
| BellaGel textured shape implant | 0.416 | 3.272 (0.188-57.075) | 0.160 | 8.308 (0.435 158.718) |
| BellaGel smooth round implant | 990 | 0.0 (0-) | 0.989 | 0.002 (0-) |
| Measures to balance both breasts | | | | |
| Breast augmentation surgery | 0.277 | 1.649 (0.669-4.061) | | |
| Mastopexy | 0.269 | 3.195 (0.408-25.041) | | |
| Breast reduction surgery | 0.983 | 0 (0-) | | |
| Adjuvant radiotherapy | 0.648 | 0.623 (0.082-4.754) | | |
| Neoadjuvant chemotherapy | 0.600 | 0.047 (0-) | | |
| Adjuvant chemotherapy | 0.237 | 0.564 (0.219-1.456) | | |
| Hormone therapy | 0.193 | 2.633 (0.612-11.325) | | |
| Interval between breast reconstruction surgeries | | | | |
| Continuous variables | 0.052 | 0.849 (0.720-1.001) | 0.034 | 0.815 (0.674-0.985) |
| Categorical variables | | | | |
| More than 6 months | Ref | | Ref | |
| 6 months or less | 0.023 | 2.796 (1.150-6.797) | 0.013 | 4.145 (1.355-12.677) |

*Period 1: stage 2 surgery performed between 2010 and 2014
**Period 2: stage 2 surgery performed between 2015 and 2018

Figure 2:
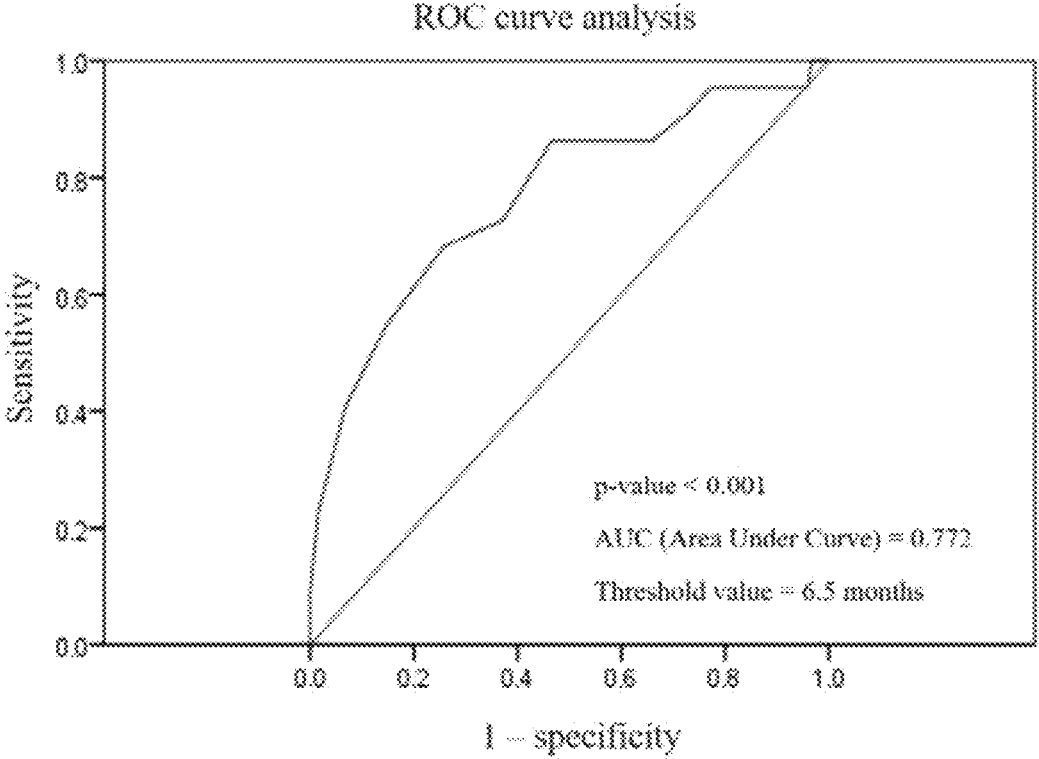
FIG. 2 shows the results of receiver operating characteristic curve (ROC curve) analysis for identifying the threshold value of the interval between the stage 1 surgery and the stage 2 surgery, which shows the greatest difference with respect to the incidence rate of implant rupture.

In order to identify the threshold value of the interval between stage 1 and stage 2s surgeries showing the greatest difference in the incidence rate of implant rupture, receiver operating characteristic curve (ROC curve) analysis was performed. Referring to FIG. 2, the area under the curve (AUC) at 6.5 months was 0.772 (p<0.001), showing maximum statistical significance.

Figure 3:
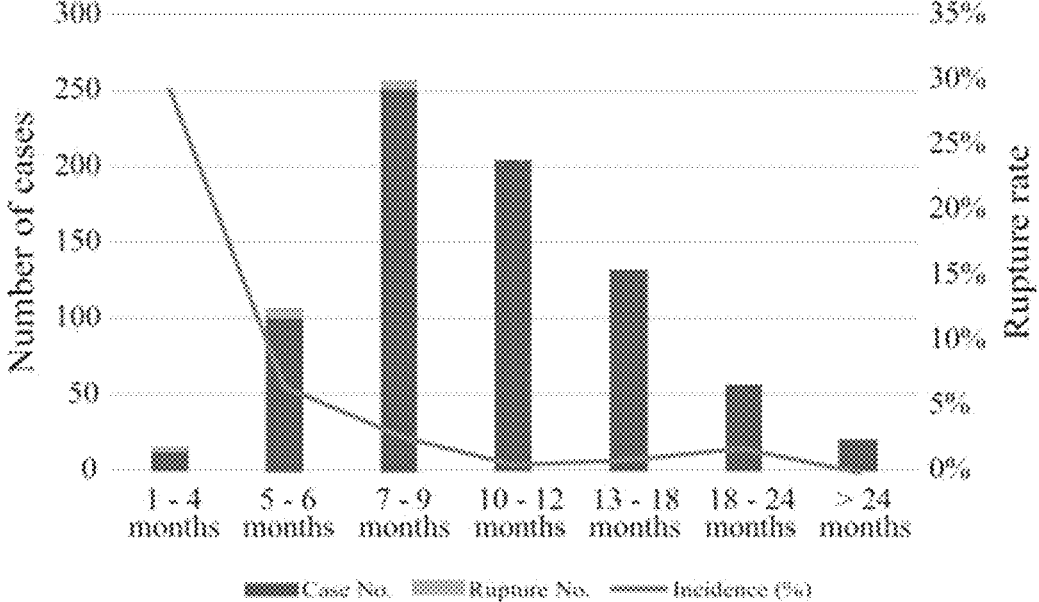
FIG. 3 shows the incidence rate of implant rupture depending on the interval between the stage 1 and stage 2 surgeries (interval between breast reconstruction surgeries).
Figure 4:
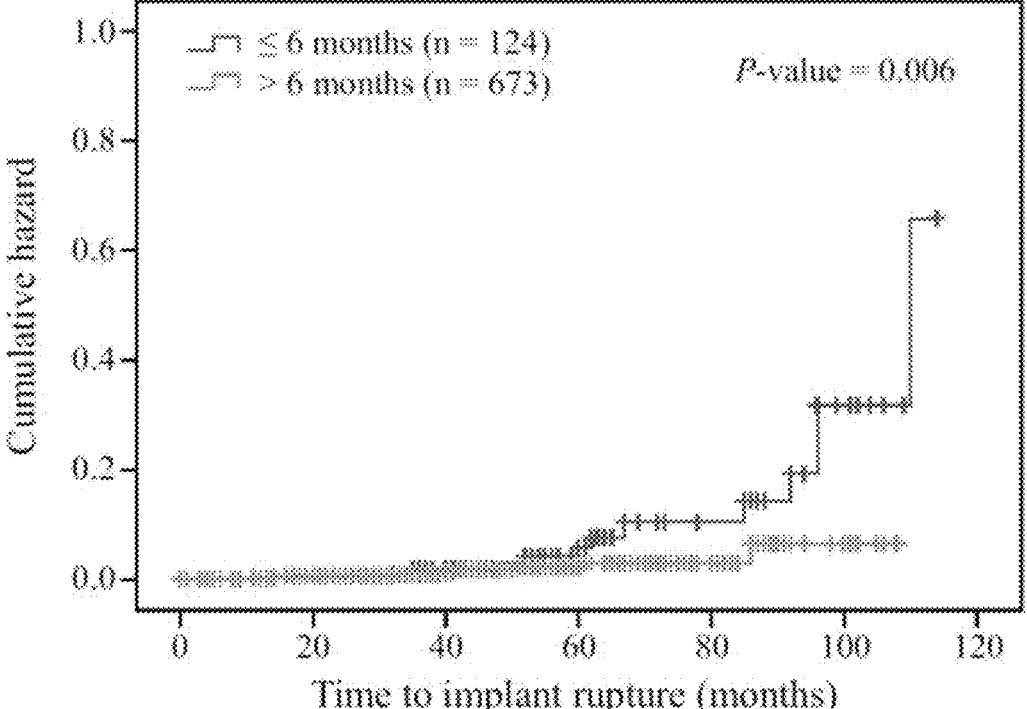
FIG. 4 shows the cumulative incidence rate of implant rupture depending on the interval between breast reconstruction surgeries.
Figure 6:
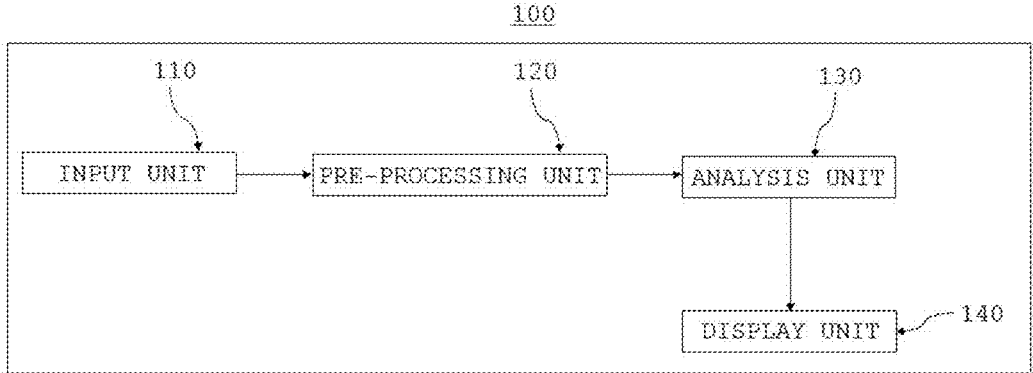
FIG. 6 is a view showing components of a system for predicting the prognosis of breast reconstruction surgery according to one specific example of the present invention.
Figure 7:
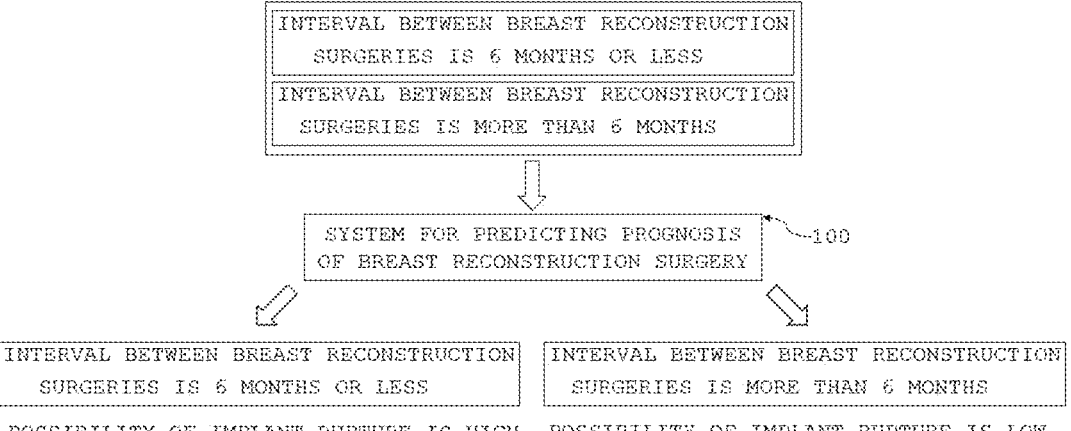
FIG. 7 is a diagram showing an example of predicting the possibility of implant rupture in a patient, who has undergone breast reconstruction surgery, depending on the interval between breast reconstruction surgeries using the system for predicting the prognosis of breast reconstruction surgery according to one specific example of the present invention.
Figure 8:
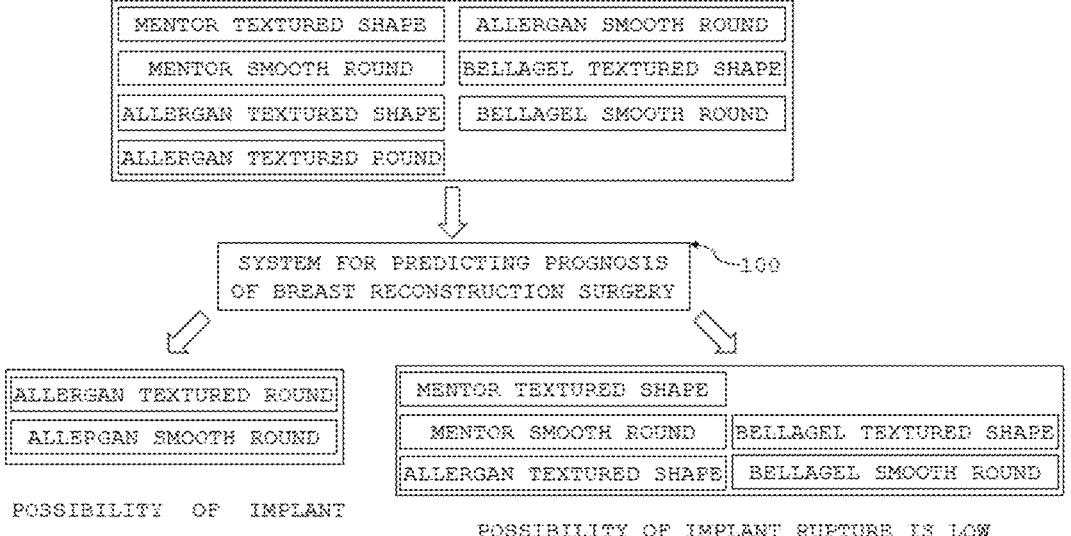
FIG. 8 is a diagram showing an example of predicting the possibility of implant rupture in a patient, who has undergone breast reconstruction surgery, depending on the type of implant implanted using the system for predicting the prognosis of breast reconstruction surgery according to one specific example of the present invention.

FIG. 3 shows the incidence rate of implant rupture depending on the interval between stage 1 surgery and stage 2 surgery. Based on these results, cases were divided into two groups based on the interval of 6.5 months. There were 124 cases where the interval was 6 months or less, and 673 cases where the interval was more than 6 months. In the Kaplan-Meier analysis, it was shown that the period during which the implant lasted without rupture was significantly different between the two groups (p=0.006) (FIG. 4). In multivariate analysis, it was shown that the possibility of implant rupture was significantly higher when the interval between breast reconstruction surgeries was 6 months or less than when the interval was more than 6 months (HR 4.45, 95% CI 1.355-12.677, p=0.013). The interval between breast reconstruction surgeries can be significantly influenced by the schedule of adjuvant therapies. At Samsung Medical Center, the stage 2 surgery was usually performed after adjuvant therapies were completed. In order to reduce related potential confounding effects, further analysis was conducted on 442 cases from which patients receiving adjuvant therapy were excluded. Results similar to those above were found, and in multivariate analysis, it was shown that the interval between stage 1 surgery and stage 2 surgery was significantly associated with implant rupture in both continuous variables (adjusted p-value=0.013, HR 0.700, 95% CI 0.527-0.929) and categorical variables (6 months or less and more than 6 months) (adjusted p-value=0.027, HR 5.152, 95% CI 1.200-22.113).

2-2-2. Type of Implant

Since the Mentor memory-shape implant was most frequently used in the study population, the Mentor memory-shape implant was used as a reference in the following analysis. Univariate Cox regression analysis results showed that the possibility of implant rupture did differ significantly depending on the type of implant. Specifically, when the Allergan Biocell textured round implant was used, the risk of implant rupture significantly increased compared to when the Mentor memory-shape implant was used (p=0.037, HR 10.520, 95% CI 1.150-96.242). This correlation was maintained even after adjusting other variables (HR 18.86, 95% CI 1.712-207.890, p=0.016). In addition, multivariate analysis showed that the risk of implant rupture significantly increased even when the Allegan smooth round implant was used (HR 13.257, 95% CI 1.463-120.127, p=0.022). Other variables, including the use of artificial dermis matrix, measures to balance both breasts, and hormone therapy did not significantly affect the results. It was shown that two types of implants had a high correlation with rupture: the non-form-stable Allegan smooth round implant and Allergan textured round implant, which are so-called 4th generation implants. Therefore, additional analysis was performed using implants divided by generation. There were 334 cases where non-form-stable 4th generation implants were used and 420 cases where form-stable 5th generation implants were used. Cases where the BellaGell implants were used were excluded from this analysis. As a result, after adjusting other variables in multivariate Cox regression analysis, it was shown that the possibility of rupture significantly increased in the cases where the 4th generation implants were used compared to the cases where the 5th generation implants were used (HR 3.793, 95% CI 1.064-13.526, p=0.040).

2-2-3. Subgroup Analysis Depending on Type (Generation) of Implant and Interval Between Breast Reconstruction Surgeries Subgroup analysis was performed to evaluate whether the effect of the interval between breast reconstruction surgeries on implant rupture differs depending on the type (generation) of implant. Among 334 cases where non-form-stable 4th generation implants were used, the interval between breast reconstruction surgeries was 6 months or less in 49 cases (14.7%), and the interval between breast reconstruction surgeries was more than 6 months in 285 cases (85.3%). Kaplan-Meier analysis showed that the period during which the implant lasted without rupture was significantly different between the two groups (p=0.014). Multivariate analysis in this subgroup study showed that, similar to the analysis results in the entire study population, the possibility of implant rupture was significantly higher in cases where the interval between breast reconstruction surgeries was 6 months or less than in cases where the interval between breast reconstruction surgeries was more than 6 months (HR 6.823, 95% CI 1.536-30.1, p=0.012). It was shown that certain types of implants were not associated with implant rupture (p=0.504).

Among 420 cases where non-form-stable 4th generation implants were used, the interval between breast reconstruction surgeries was 6 months or less in 70 cases (16.7%), and the interval between breast reconstruction surgeries was more than 6 months in 350 cases (83.3%). The two groups showed similar cumulative incidence rates in Kaplan-Meier analysis (p=0.941). Multivariate analysis showed that the interval between breast reconstruction surgeries did not significantly affect the incidence rate of implant rupture (p=0.635).

In summary, according to the judgment criteria derived in the above-described examples, it is possible to provide information and a system, which predict the possibility of implant rupture after stage 2 surgery depending on the interval between breast reconstruction surgeries and the type of implant implanted in a patient undergoing two-stage breast reconstruction surgery.

So far, the present invention has been described with reference to the preferred embodiments. Those skilled in the art will appreciate that the present invention can be implemented in modified forms without departing from the essential features of the present invention. Therefore, the disclosed embodiments should be considered in descriptive sense only and not for purposes of limitation. Therefore, the scope of the present invention is defined not by the detailed description of the present invention but by the appended claims, and all differences within a range equivalent to the scope of the appended claims should be construed as being included in the present invention.

DESCRIPTION OF REFERENCE NUMERALS

100: prediction system

110: input unit

120: pre-processing unit

130: analysis unit

140: display unit

The invention claimed is:

1. A method of providing information to predict a prognosis of breast reconstruction surgery, comprising:

collecting clinical data;

calculating a pattern including a same result by classifying the clinical data on a basis of an interval between breast reconstruction surgeries, type of implant implanted, and whether the implant has ruptured; and predicting possibility of implant rupture in a subject by applying an interval between breast reconstruction surgeries or a type of implant implanted, among clinical data of the subject to the calculated pattern.

2. The method of claim 1, wherein the breast reconstruction surgery is a two-stage breast reconstruction surgery comprising:

inserting a tissue expander; and exchanging the tissue expander for an implant.

3. The method of claim 1, wherein the interval between breast reconstruction surgeries is 6 months or less or more than 6 months.

4. The method of claim 1, wherein in the predicting the possibility of implant rupture, when the interval between breast reconstruction surgeries is 6 months or less, the possibility of implant rupture is predicted to be high.

5. The method of claim 1, wherein the type of the implant is any one implant selected from the group consisting of Mentor textured shape, Mentor smooth round, Allergan textured shape, Allergan textured round, Allergan smooth round, BellaGel textured shape, and BellaGel smooth round.

6. The method of claim 1, wherein in the predicting the possibility of implant rupture, when the type of the implant is Allergan textured round or Allergan smooth round, the possibility of implant rupture is predicted to be high.

7. A system for predicting prognosis of breast reconstruction surgery, comprising:

an input unit configured to receive clinical data;

a pre-processing unit configured to calculate a pattern including a same result by classifying the clinical data on a basis of an interval between breast reconstruction surgeries, type of implant implanted, and whether the implant has ruptured; and an analysis unit configured to predict possibility of implant rupture in a subject by applying an interval between breast reconstruction surgeries or a type of implant implanted, among clinical data of the subject to the calculated pattern.

8. The system of claim 7, wherein the breast reconstruction surgery is a two-stage breast reconstruction surgery comprising:

inserting a tissue expander; and exchanging the tissue expander for an implant.

9. The system of claim 7, wherein the interval between breast reconstruction surgeries is 6 months or less or more than 6 months.

10. The system of claim 7, wherein in the predicting the possibility of implant rupture, when the interval between breast reconstruction surgeries is 6 months or less, the possibility of implant rupture is predicted to be high.

11. The system of claim 7, wherein the type of the implant is any one implant selected from the group consisting of Mentor textured shape, Mentor smooth round, Allergan textured shape, Allergan textured round, Allergan smooth round, BellaGel textured shape, and BellaGel smooth round.

12. The system of claim 7, wherein in the predicting the possibility of implant rupture, when the type of the implant is Allergan textured round or Allergan smooth round, the possibility of implant rupture is predicted to be high.

13. The system of claim 7, wherein the analysis unit predicts that the possibility of implant rupture is high when the interval between breast reconstruction surgeries is 6 months or less.

14. The system of claim 7, wherein the analysis unit predicts that the possibility of implant rupture is high when the type of the implant implanted into the subject is Allergan textured round or Allergan smooth round.

15. The system of claim 7, further comprising a display unit configured to output the result of predicting the possibility of implant rupture of the subject in the analysis unit.

* * * * *